(12) United States Patent
Cotter et al.

(10) Patent No.: US 9,931,618 B2
(45) Date of Patent: Apr. 3, 2018

(54) ALKALI METAL-MODIFIED VANADIUM-PHOSPHORUS OXIDE (VPO) CATALYST

(71) Applicants: Thomas Cotter, Munich (DE); Andreas Reitzmann, Stephanskirchen (DE); Gerhard Mestl, Munich (DE); Gabriele Donabauer, Bruckmuehl (DE); Susanne Roehrer, Bad Aibling (DE)

(72) Inventors: Thomas Cotter, Munich (DE); Andreas Reitzmann, Stephanskirchen (DE); Gerhard Mestl, Munich (DE); Gabriele Donabauer, Bruckmuehl (DE); Susanne Roehrer, Bad Aibling (DE)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 14/673,569

(22) Filed: Mar. 30, 2015

(65) Prior Publication Data

US 2015/0283538 A1 Oct. 8, 2015

(30) Foreign Application Priority Data

Apr. 2, 2014 (DE) .................. 10 2014 004 786

(51) Int. Cl.

| | | |
|---|---|---|
| *B01J 27/199* | (2006.01) | |
| *B01J 27/198* | (2006.01) | |
| *B01J 37/28* | (2006.01) | |
| *C07D 307/60* | (2006.01) | |
| *B01J 37/10* | (2006.01) | |
| *B01J 23/00* | (2006.01) | |
| *B01J 37/00* | (2006.01) | |

(52) U.S. Cl.
CPC ............ *B01J 27/199* (2013.01); *B01J 23/002* (2013.01); *B01J 27/198* (2013.01); *B01J 37/0063* (2013.01); *B01J 37/10* (2013.01); *B01J 37/28* (2013.01); *C07D 307/60* (2013.01); *B01J 2523/00* (2013.01)

(58) Field of Classification Search
CPC ...... B01J 27/198; B01J 27/199; C07D 307/34
USPC ........ 502/209, 211, 212; 549/256, 258, 259, 549/262
See application file for complete search history.

(56) References Cited

U.S. PATENT DOCUMENTS

| | | | |
|---|---|---|---|
| 2,967,185 A | 1/1961 | Becker et al. | |
| 3,156,706 A | 11/1964 | Ralph | |
| 3,288,721 A * | 11/1966 | Kerr ....................... | B01J 27/198 502/209 |
| 4,018,709 A | 4/1977 | Barone et al. | |
| 4,097,498 A * | 6/1978 | Barone ................. | B01J 23/002 502/202 |
| 4,172,084 A * | 10/1979 | Bremer ................. | B01J 23/002 502/209 |
| 4,219,484 A * | 8/1980 | Milberger ............. | B01J 23/002 502/209 |
| 4,251,390 A | 2/1981 | Barone | |
| 4,652,543 A * | 3/1987 | Edwards ............... | B01J 23/002 423/305 |
| 4,760,153 A | 7/1988 | Takahashi et al. | |
| 4,795,818 A | 1/1989 | Beaker et al. | |
| 4,996,179 A * | 2/1991 | Haddad ................. | B01J 23/002 502/209 |
| 5,070,060 A | 12/1991 | Barone | |
| 5,158,923 A | 10/1992 | Barone | |
| 5,275,996 A | 1/1994 | Andrews et al. | |
| 5,296,436 A | 3/1994 | Bortinger | |
| 5,480,853 A | 1/1996 | Bortinger | |
| 5,521,134 A | 5/1996 | Bortinger et al. | |
| 5,780,656 A | 7/1998 | Rizkalla et al. | |
| 5,885,919 A | 3/1999 | Bortinger | |
| 5,922,637 A | 7/1999 | Bortinger | |
| 5,929,256 A * | 7/1999 | Felthouse ............. | C07C 51/215 549/260 |
| 6,093,835 A * | 7/2000 | Sawaki ................. | C07C 51/215 549/256 |
| 6,107,234 A | 8/2000 | Bortinger | |
| 6,858,561 B2 | 2/2005 | Bortinger et al. | |
| 7,294,317 B2 | 11/2007 | Billig et al. | |
| 7,619,099 B2 | 11/2009 | Padia et al. | |
| 7,629,286 B2 † | 12/2009 | Haddad | |
| 8,048,820 B2 | 11/2011 | Brandstädter et al. | |

(Continued)

FOREIGN PATENT DOCUMENTS

| | | | |
|---|---|---|---|
| CN | 10-1155638 | * | 4/2008 |
| CN | 101155638 | | 4/2008 |
| CN | 101300073 | | 11/2008 |
| DE | 2611290 | | 9/1976 |
| DE | 3018849 | | 12/1980 |
| DE | 102005056866 | | 5/2007 |
| DE | 102010040921 | | 3/2012 |
| DE | 102013008207 | | 11/2014 |
| EP | 0458541 | | 11/1991 |
| EP | 0975615 | | 2/2000 |
| EP | 1358441 | | 11/2003 |
| JP | S6278 | | 1/1987 |
| JP | H1142134 | | 2/1999 |
| JP | 2003523813 | | 8/2003 |
| WO | WO 99/08143 | | 2/1999 |
| WO | WO 00/44494 | | 8/2000 |
| WO | WO 20004/103557 | | 12/2004 |

OTHER PUBLICATIONS

Erigfish Abstract for JPS6278, dated Jan. 6, 1987.
English Abstract for JPH1142434, dated Feb. 16, 1999.
German Search Report for DE 10 2014 004 786.5, dated Mar. 16, 2015.
Machine English Translation of abstract, description, claims and single drawing sheet for CN 101300073, dated May 11, 2008.

*Primary Examiner* — Patricia L Hailey
(74) *Attorney, Agent, or Firm* — Anthony A. Bisulca

(57) ABSTRACT

The present invention relates to a catalyst containing a vanadium-phosphorus oxide and an alkali metal, wherein the proportion by weight of alkali metal in the vanadium-phosphorus oxide is in the range from 10 to 400 ppm, based on the total weight of the vanadium-phosphorus oxide, a process for producing it and also the use of the catalyst for the gas-phase oxidation of hydrocarbons, in particular for preparing maleic anhydride.

12 Claims, No Drawings

(56) References Cited

U.S. PATENT DOCUMENTS

| | | |
|---|---|---|
| 8,877,966 B2 | 11/2014 | Herzog et al. |
| 9,409,160 B2 | 8/2016 | Reitzmann et al. |
| 9,539,562 B2 | 1/2017 | Bentele et al. |
| 2006/0247447 A1* | 11/2006 | Haddad ................. B01J 23/002 549/259 |
| 2009/0306410 A1* | 12/2009 | Brandstadter ............ B01J 19/30 549/262 |
| 2013/0338378 A1* | 12/2013 | Reitzmann ............. B01J 35/026 549/259 |
| 2014/0343319 A1 | 11/2014 | Goebel et al. |
| 2016/0030937 A1 | 2/2016 | Gabriel |

\* cited by examiner
† cited by third party

ALKALI METAL-MODIFIED VANADIUM-PHOSPHORUS OXIDE (VPO) CATALYST

The present invention relates to a catalyst containing a vanadium-phosphorus oxide (VPO catalyst) and an alkali metal, wherein the proportion by weight of alkali metal in the vanadium-phosphorus oxide is in the range from 10 to 400 ppm, based on the total weight of the vanadium-phosphorus oxide, a process for producing it and also the use of the catalyst for the gas-phase oxidation of hydrocarbons, in particular for preparing maleic anhydride.

Maleic anhydride is a chemical intermediate of great economic importance. It is used, for example, in the preparation of alkyd and polyester resins either alone or in combination with other acids. In addition, it is also a versatile intermediate for chemical synthesis, for example for the synthesis of γ-butyrolactone, tetrahydrofuran and 1,4-butanediol, which in turn are used as solvents or can be processed further to give polymers, for example polytetrahydrofuran or polyvinyl-pyrrolidone.

Maleic anhydride is generally prepared by partial oxidation of hydrocarbons in the gas phase by means of molecular oxygen or by means of a gas containing molecular oxygen in the presence of a vanadium-phosphorus oxide catalyst (VPO catalyst). In general, the oxidation catalysts contain mixed oxides of vanadium and phosphorus, with oxidation catalysts of this type containing vanadium in a valence of from +3.8 to +4.8 having been found to be particularly useful for the preparation of maleic anhydride from saturated hydrocarbons having at least four carbon atoms. Both fixed-bed reactors and fluidized-bed reactors are used.

All VPO catalysts used industrially are produced from vanadium-phosphorus oxides, in particular vanadium pyrophosphates. For this purpose, a reduction of vanadium pentoxide ($V_2O_5$) and subsequent reaction with phosphoric acid ($H_3PO_4$) is usually carried out in an organic alcoholic solvent.

The VPO catalysts displaying the best performance at present are installed over a length of from 3 to 6 meters in fixed-bed reactors in the preparation of maleic anhydride and are operated in the temperature range from 390 to 420° C. at space velocities of from 1800 to 2000 $h^{-1}$ (from 1.8 to 2% of $C_4$) to give degrees of conversion of from 83 to 86%. The selectivities achieved under these conditions are usually in the range from 73 to 77%, so that a total yield of from about 62 to 65 mol % (corresponding to from about 105 to 110% by weight) can be achieved. Over an expected life of four years, the catalysts usually achieve a conversion into maleic anhydride of 4000 kilogram per kilogram of catalyst.

VPO catalysts have only a low intrinsic activity in the reaction of n-butane to form maleic anhydride. A large amount of catalyst is therefore required for a satisfactory conversion. In addition, VPO catalysts are among the most expensive non-noble metal catalysts, essentially because of the high costs of their starting materials. As a result, it is an important objective to improve the catalyst performance (activity and selectivity) and also life of such catalysts.

It was therefore an object of the present invention to provide a VPO catalyst for the gas-phase oxidation of hydrocarbons, in particular for preparing maleic anhydride, which has improved catalysis performance, i.e. degree of conversion and selectivity.

This object is achieved by a catalyst containing a vanadium-phosphorus oxide and an alkali metal, wherein the proportion by weight of alkali metal in the vanadium-phosphorus oxide is in the range from 10 to 400 ppm (parts per million), based on the total weight of the vanadium-phosphorus oxide.

The inventors of the present patent application have surprisingly found that a small amount of alkali metal in the vanadium-phosphorus oxide significantly increases the degree of conversion and selectivity, in particular the selectivity, in the use as catalyst for the oxidation of hydrocarbons. However, an even lower content of alkali metal has no effects with regard to improving the performance. When the content of alkali metal is too high, it appears that poisoning of the catalyst occurs, so that the performance of the catalyst is greatly decreased again.

For the purposes of the present application, the term "vanadium-phosphorus oxide" refers to any mixed oxide of vanadium, phosphorus and optionally further elements of the Periodic Table.

In the present patent application, the amount indicated in ppm is ppm by weight (wt. ppm), i.e. 1 ppm means $1/1\,000\,000$ (1 millionth) of the weight of the vanadium-phosphorus oxide.

In a further embodiment of the present patent application, preference is given to the catalyst consisting of the vanadium-phosphorus oxide.

In a further embodiment of the present patent application, preference is given to the proportion of alkali metal in the catalyst of the invention being in the range from 20 to 350 ppm, more preferably in the range from 50 to 320 ppm and most preferably in the range from 80 to 300 ppm.

The alkali metal is preferably homogeneously distributed in the vanadium-phosphorus oxide, i.e. the vanadium-phosphorus oxide is preferably present as mixed oxide of the alkali metal, vanadium and phosphorus, with the mixed oxide being able to contain further elements in addition to the elements mentioned.

The term alkali metal refers to a metal selected from the group consisting of Li, Na, K, Rb, Cs and mixtures thereof. Greater preference is given to the alkali metal being Na, K, Rb, Cs or a mixture thereof. Even more preferably, the alkali metal is Na, K or a mixture thereof.

In a further embodiment, the catalyst of the invention can contain molybdenum and/or bismuth, preferably in oxidic form. However, the molybdenum and/or bismuth is preferably part of the catalytically active vanadium-phosphorus oxide and is likewise present in oxidic form, i.e. the vanadium-phosphorus oxide is preferably doped with molybdenum or bismuth. In this case, the doped vanadium-phosphorus oxide preferably comprises the molybdenum and/or the bismuth in an amount in the range from 0.10 to 0.90% by weight of molybdenum and/or from 0.10 to 1.5% by weight of bismuth and more preferably in the range from 0.20 to 0.60% by weight of molybdenum and/or from 0.5 to 1.3% by weight of bismuth, based on the total weight of the doped vanadium-phosphorus oxide.

In a further embodiment, the vanadium-phosphorus oxide in the catalyst of the invention is free of Zn and/or Ni.

The VPO catalyst of the invention can be used both in fixed-bed reactors and in fluidized-bed reactors. In one embodiment, the VPO catalyst is configured as shaped body which is suitable for a fixed-bed reactor. For this purpose, the VPO catalyst of the invention can be shaped with compaction by means of apparatuses with which a person skilled in the art would be familiar, for example tableting presses or extruders, and subsequently calcined to give a stable shaped body. Possible shaped bodies are, for example, balls, pellets, cylinders, rings or the shaped bodies disclosed in DE 102005056866 A1.

In other words, the present invention also provides a process for producing a catalyst according to the invention, wherein either a vanadium source and an alkali metal source or an alkali metal-containing vanadium source is reacted with a phosphorus source, where the proportion of alkali metal is selected so that the vanadium-phosphorus oxide has a proportion by weight of alkali metal in the range from 10 to 400 ppm, more preferably from 20 to 350 ppm, even more preferably from 50 to 320 ppm and most preferably from 80 to 300 ppm, based on the total weight of the vanadium-phosphorus oxide.

The content of alkali metal in the vanadium-phosphorus oxide of the catalyst of the invention can, in the process of the invention, be controlled in a simple manner via the weight of the sources necessary for the synthesis. It is assumed here that the alkali metal source and vanadium source used or the alkali metal-containing vanadium source used react quantitatively to form the end product. Otherwise, the final content can also be determined by elemental analysis (AAS or ICP).

The synthesis of the vanadium-phosphorus oxide can be carried out in a conventional manner. As vanadium source, preference is given to using a high-valence vanadium compound, e.g. vanadium pentoxide ($V_2O_5$), and phosphoric acid ($H_3PO_4$) is preferably used as phosphorus source. For this purpose, preference is given to the high-valence vanadium compound being subjected to a reduction in a first step and the compound obtained therefrom being reacted with the phosphorus source, preferably in an organic alcoholic solvent, in a second step. In the embodiment in which an alkali metal source is reacted with a vanadium source and a phosphorus source, the alkali metal source is preferably added either during the reduction of the vanadium source or subsequently during the step of reaction with the phosphorus source.

It is possible to use aliphatic or aromatic alcohols as reducing agent for the reduction of a high-valence vanadium compound in the abovementioned first step. Examples are: methanol, ethanol, n-propanol, i-propanol, n-butanol, 2-butanol and benzyl alcohol.

As alkali metal source, it is possible to use, for example, inorganic or organic salts, with inorganic salts being preferred. The inorganic salts are preferably selected from among the following compounds: carbonates, hydrogencarbonates, phosphates, hydrogen phosphates, dihydrogen phosphates, silicates and nitrates.

Further process steps, for example a mechanical treatment, drying, in particular spray drying, spray coating, extrusion and calcination, are possible.

The present invention further provides for the use of a VPO catalyst according to the invention for the (gas-phase) oxidation of hydrocarbons. In other words, the present invention also provides a process for the (gas-phase) oxidation of hydrocarbons using a VPO catalyst according to the invention.

Furthermore, the present invention provides for the use of a VPO catalyst according to the invention for preparing maleic anhydride by gas-phase oxidation of hydrocarbons having at least four carbon atoms, in particular n-butane.

The present invention further provides a process for preparing maleic anhydride by gas-phase oxidation of hydrocarbons having at least four carbon atoms, in particular n-butane, wherein the oxidation takes place in the presence of a VPO catalyst according to the invention. Fixed-bed reactors are preferably used here.

As hydrocarbons, use is usually made of aliphatic or aromatic, saturated or unsaturated hydrocarbons having at least four carbon atoms, for example 1,3-butadiene, 1-butene, cis-2-butene, trans-2-butene, n-butane, 1,3-pentadiene, 1,4-pentadiene, 1-pentene, cis-2-pentene, trans-2-pentene, n-pentane, cyclopentadiene, dicyclo-pentadiene, cyclopentene, cyclopentane, hexene, hexane, cyclohexane and/or benzene. Preference is given to using 1-butene, cis-2-butene, trans-2-butene, n-butane, benzene or mixtures thereof. The use of n-butane and n-butane-containing gases and liquids is particularly preferred.

As oxidant, use is usually made of oxygen-containing gases, for example air, synthetic air, a gas enriched with oxygen or pure oxygen.

In a preferred embodiment, the catalyst of the invention is brought into contact with a gas having a hydrocarbon concentration of from 0.5 to 15% by volume and an oxygen concentration of from 8 to 25% by volume. The remainder of the gas is made up of further gases such as nitrogen, noble gases, carbon monoxide, carbon dioxide and mixtures thereof. The proportion of n-butane in the total amount of hydrocarbon is preferably more than 90% and particularly preferably more than 95%.

The process of the invention is generally carried out at a temperature of from 350 to 480° C. The process of the invention is preferably carried out at a temperature of from 380 to 460° C., in particular from 380 to 440° C.

The use of the catalysts according to the invention improves the economics of the process of the invention compared to conventional processes for preparing maleic anhydride.

Some examples which illustrate the invention in conjunction with Table 1 but do not restrict the scope of the invention are described below.

Tab. 1 summarizes the course of the selectivity to maleic anhydride ([%]) at an 85% $C_4$ conversion for Examples 1-3 according to the invention and comparative examples 1 and 2.

EXAMPLE 1

Catalyst A According to the Invention (80 ppm of Na)

Laboratory Synthesis of the Hemihydrates ($VMo_{0.0088}OHPO_4 \lambda 0.5H_2O$):

A heating mantle is placed on a lab jack and a 2 l four-neck flask is located in this. A half-moon stirrer having a close-fitting stirring connection which is connected by means of a stirrer coupling to the stirring device is located in the middle opening of the four-neck flask. In the right-hand opening, there is a thermometer, while a riser tube to the reflux condenser is located in the left-hand opening. The opening at front in the middle is used for charging with the chemicals, and the nitrogen flushing is then connected there. The entire apparatus can also be flooded with nitrogen. For this purpose, the nitrogen is firstly conveyed through a gas wash bottle and then into the apparatus and discharged at the top from the cooler, once again through a gas wash bottle.

Firstly, isobutanol, 1069.5 g, and benzyl alcohol, 156.0 g, are introduced. While stirring, $V_2O_5$, 150 g, is added. After the $V_2O_5$ addition, 2.52 g of ammonium dimolybdate (as an alternative or in addition, 12.18 g of bismuth ethylhexanoate can be used) and 0.0468 g of sodium carbonate are added. Phosphoric acid, 232.50 g, is subsequently added to the suspension and the mixture is refluxed under $N_2$ for 14-18 hours.

Filtration:

After cooling of the suspension, the latter is transferred from the four-neck flask to a suction filter and the liquid is removed under suction. The moist filter cake is pressed dry overnight in a press at 14-18 bar.

Drying:

The pressed filter cake is placed in the evaporator flask of a rotary evaporator. The filter cake is dried overnight at 100° C. under a water pump vacuum.

Calcination:

The dried powder is put in a suitable calcination pot and placed in an oven and calcined at temperatures of from 200 to 300° C. in an atmosphere of 4-6% of $O_2$ in $N_2$ for 9 hours.

Tableting:

Before compaction/tableting, 5% by weight of graphite are added to the calcined catalyst precursor powder and homogeneously mixed by means of a drum hoop mixer. This powder is compacted to form plates by means of a roller compactor having a pressing pressure of 190 bar, a gap width of 0.60 mm and a roller speed of 7 rpm and granulated through a 1 mm sieve.

The granulated material is pressed by means of a rotary tableting press to produce the desired pellet shape, with appropriate height, e.g. 5.5×5.5×2.3 mm or 4.7×4.7×1.5 mm (height×external diameter×internal diameter) and lateral compressive strength.

Activation/synthesis of the Pyrophosphate:

The synthesis of the vanadium pyrophosphate is carried out under controlled conditions in a retort installed in a programmable oven. The amount of calcined tablets allowed on the basis of the C content is introduced uniformly into the retort and the latter is closed tightly. The catalyst is then activated in a humid air/nitrogen mixture (60% absolute atmospheric humidity) firstly at 300° C. for 5 hours and subsequently at 400° C. for 9 hours.

EXAMPLE 2

Catalyst B According to the Invention (160 ppm of Na)

A catalyst B is produced as described in Example 1 with the only difference that this catalyst has a sodium content of 160 ppm. For this purpose, the above-described synthesis is modified in that 0.0937 g of sodium carbonate are added together with ammonium dimolybdate.

EXAMPLE 3

Catalyst C According to the Invention (300 ppm of Na)

A catalyst C is produced as described in Example 1 with the only difference that this catalyst has a sodium content of 300 ppm. For this purpose, the above-described synthesis is modified in that 0.1756 g of sodium carbonate are added together with ammonium dimolybdate.

EXAMPLE 4

Comparative Catalyst D (<10 ppm of Na)

A catalyst D is produced as described in Example 1 with the only difference that no sodium compound is added.

EXAMPLE 5

Comparative Catalyst E (500 ppm of Na)

A catalyst E is produced as described in Example 1 with the only difference that this catalyst has a sodium content of 500 ppm. For this purpose, the above-described synthesis is modified so that 0.2927 g of sodium carbonate are added together with ammonium dimolybdate.

EXAMPLE 6

Determination of the Catalytic Performances Of the Illustrative Catalysts A with E In each case 67-69 g of the catalysts produced in Examples A-C according to the invention and the Comparative Examples D and E are diluted with inert steatite rings in a weight ratio of inert material to catalyst of 4:1 and introduced into the isothermal region of a test reactor (21 mm tube diameter, 1.2 m length) heated by means of molten salt. The molybdenum-containing catalysts and comparative catalysts were used in each case. The temperature profile of the diluted catalyst bed is checked by means of a multipoint type K thermocouple. The catalysts are subsequently brought to equilibrium with an air-butane mixture (1.5% by volume of butane, air 98.5% by volume) at a total pressure of 1.1 bar over a period of 72 hours at a salt bath temperature of 410° C. (equilibration step), before the catalytic measurements are carried out. The catalytic measurements are carried out at two different salt bath temperatures (380° C. and 410° C.) in the same air/butane mixture as in the equilibration step and at a total pressure of 1.1 bar and at space velocities in a range of 1250, 1800, 2500, 3500, 5500 l/kg/h. Both an infrared spectrometer (for determining the butane, carbon monoxide and carbon dioxide contents) and a gas chromatograph (for determining the maleic anhydride, acrylic acid and acetic acid contents) are used for analysis.

Test Results:

The performances of the catalysts A-C according to the invention and the Comparative Examples D and E in the catalytic conversion of n-butane into maleic anhydride are summarized in Tab. 1.

TABLE 1

Comparison of the catalytic performances of the catalysts A with E

| Sample | Na content (ppm) | $C_4$ conversion (%) | Selectivity to MAn (%) |
|---|---|---|---|
| Example 4, catalyst D | <10 | 85 | 64.9 |
| Example 1, catalyst A | 80 | 85 | 65.5 |
| Example 2, catalyst B | 160 | 85 | 66.1 |
| Example 3, catalyst C | 300 | 85 | 66.3 |
| Example 5, catalyst E | 500 | 85 | 64.5 |

The invention claimed is:

1. A catalyst comprising a vanadium-phosphorus oxide and an alkali metal selected from the group consisting of sodium, potassium and mixtures thereof, wherein the proportion by weight of alkali metal in the vanadium-phosphorus oxide is in the range from 10 to 400 ppm and wherein the vanadium-phosphorus oxide contains 0.10 to 0.90 w.t.-% molybdenum, based on the total weight of the vanadium-phosphorus oxide, respectively.

2. The catalyst as claimed in claim 1, wherein the proportion of alkali metal is in the range from 80 to 300 ppm.

3. The catalyst as claimed in claim 1, wherein the alkali metal is homogeneously distributed in the vanadium-phosphorus oxide.

4. The catalyst as claimed in claim 1, wherein the vanadium-phosphorus oxide is present as a mixed oxide of the alkali metal, vanadium and phosphorus.

5. The catalyst as claimed in claim 1, wherein the vanadium-phosphorus oxide is free of Zn and/or Ni.

6. The catalyst as claimed in claim , wherein the catalyst consists of the vanadium-phosphorus oxide.

7. A process for producing a catalyst as claimed in claim 1 comprising the step of reacting either a vanadium source and an alkali metal source or an alkali metal-containing vanadium source with a phosphorus source, wherein the alkali metal is selected from the group consisting of sodium, potassium and mixtures thereof, where the proportion of alkali metal is selected so that the vanadium-phosphorus oxide has a proportion by weight of alkali metal in the range from 10 to 400 ppm and wherein the vanadium-phosphorus oxide contains 0.10 to 0.90 w.t.-% molybdenum, based on the total weight of the vanadium-phosphorus oxide, respectively.

8. A catalyst for the gas-phase oxidation of a hydrocarbon comprising a vanadium-phosphorus oxide and an alkali metal, wherein the alkali metal is selected from the group consisting of sodium, potassium and mixtures thereof, wherein the proportion by weight of alkali metal in the vanadium-phosphorus oxide is in the range from 10 to 400 ppm and wherein the vanadium-phosphorus oxide contains 0.10 to 0.90 w.t.-% molybdenum, based on the total weight of the vanadium-phosphorus oxide, respectively.

9. The catalyst as claimed in claim 8, wherein the hydrocarbon is passed over the catalyst.

10. The catalyst as claimed in claim 8, wherein the hydrocarbon has at least 4 carbon atoms.

11. The catalyst as claimed in claim 8, wherein the hydrocarbon is n-butane.

12. The catalyst as claimed in claim 8, wherein maleic anhydride is formed in the (gas-phase) oxidation.

* * * * *